United States Patent [19]

Philippe

[11] Patent Number: 5,412,125
[45] Date of Patent: May 2, 1995

[54] DIPEPTIDIC AMIDES DERIVED FROM GLYCYL-SERINE AS SURFACTANTS OR HYDRATING AGENTS AND COSMETIC, PHARMACEUTICAL OR ALIMENTARY COMPOSITIONS CONTAINING THE SAME

[75] Inventor: Michel Philippe, Antony, France
[73] Assignee: L'Oreal, Paris, France
[21] Appl. No.: 36,265
[22] Filed: Mar. 24, 1993

Related U.S. Application Data

[62] Division of Ser. No. 828,662, Feb. 6, 1992, Pat. No. 5,234,909.

[30] Foreign Application Priority Data

Feb. 6, 1991 [FR] France ............... 91 01308

[51] Int. Cl.$^6$ ............................................. C07K 5/062
[52] U.S. Cl. .................................................. 554/35
[58] Field of Search ................ 562/564; 554/110, 35

[56] References Cited

FOREIGN PATENT DOCUMENTS 0054435 6/1982 European Pat. Off. ... C07C 103/52
61-257823 10/1986 Japan.
62-126384 5/1987 Japan.
62-255810 10/1987 Japan.
0112909 6/1992 Japan .............................. A61K 7/00

OTHER PUBLICATIONS

Shoji et al., *Chemical Abstracts*, Nos. 112(9):69993z (1989).
Shoji et al., *Chemical Abstracts*, vol. 112, No. 7, abs. 48768q, 1989.
Shoji et al., *Chemical Abstracts*, vol. 109, No. 25, abs. 231563w, 1988.
Patent Abstracts of Japan, vol. 10, No. 303 (C–378) (2359), Oct. 1986, "Fat–soluble sericinpeptide–containing cosmetic".

*Primary Examiner*—Raymond Henley, III
*Assistant Examiner*—William R. A. Jarvis
*Attorney, Agent, or Firm*—Cushman Darby & Cushman

[57] ABSTRACT

This invention relates to a dipeptidic amide having the formula $RCO-NHCH_2CONH-CH(CH_2OH)-COOH$ wherein R is an oleoyl group. The compound is useful in cosmetic and pharmaceutical compositions for the treatment or care of the skin.

1 Claim, No Drawings

DIPEPTIDIC AMIDES DERIVED FROM GLYCYL-SERINE AS SURFACTANTS OR HYDRATING AGENTS AND COSMETIC, PHARMACEUTICAL OR ALIMENTARY COMPOSITIONS CONTAINING THE SAME

This application is a divisional of application Ser. No. 828,662 filed Feb. 6, 1992, now U.S. Pat. No. 5,234,909.

The present invention relates to the use of, as surface active agents or as hydrating agents, principally in cosmetic, hygienic, pharmaceutical or alimentary compositions, certain dipeptidic amides derived from glycyl-serine.

It is already known that dipeptidic amides, derived from glycyl-glycine can be used as surfactant agents; see Japanese patent application 84994/1984.

Further, it is also known that N-tetradecanoyl-glycylserine has been described as a cellular proliferation inhibitor in Japanese patent application 146851/1988.

It has now been discovered that, in a surprising manner, amides derived from glycyl-serine have surfactant properties which are particularly superior to those of corresponding amides derived from glycyl-glycine.

Moreover, certain amides derived from glycyl-serine have a hydrating effect when they are present in dermo-pharmaceutical compositions or in cosmetic composition for the skin.

The invention thus related to the use, as surfactant agents and/or as hydrating agents, of dipeptidic amides of general formula I:

RCO—NHCH$_2$CONH—CH(CH$_2$OH)—COOH     (I)

wherein R represents a linear or branched alkyl, optionally unsaturated, having 2-17 carbon atoms, as well as salts of the compounds of formula I, and mixtures of compounds of formula (I) and/or their salts.

The compounds of formula I can be derived from D-, L- or D,L-serine.

Among the compounds of formula I useful in accordance with the invention mention in particular can be made of those for which the hydrocarbon radical R represents a saturated alkyl radical, and those for which R represents an alkyl radical having 1 to 3 ethylenic double bonds. Preferably, R has from 7 to 17 carbon atoms. The R group is selected, for example, in a manner such that RCO represents an octanoyl, decanoyl, dodecanoyl, tetradecanoyl, oleoyl, linoleoyl group, etc.

Among the salts of the compounds of formula I (carboxylates), mention can principally be made of salts compatible with the desired use, that is to say, according to the situation, with oral administration, or with application to the skin or mucous. The salts compatible with these various uses are known, or can be easily determined by routine experimentation—for example, salts compatible with application to the skin or mucous are principally metallic salts such as sodium, zinc, magnesium, aluminum and copper (II) salts or salts having organic cations such as salts of a quaternary ammonium having the formula

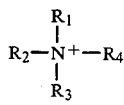

(Ia)

wherein $R_1$, $R_2$, $R_3$ and $R_4$, each independently, represent a —CH$_3$, —CH$_2$—C$_6$H$_5$ or —CH$_2$—CH$_2$OH group.

By convention, the term "compounds" or "derivatives" of formula I designate hereafter the compounds of formula I and/or their salts.

The invention then principally relates to the use of compounds of formula I, and their salts, as surfactant agents, principally in cosmetic, hygienic or dermopharmaceutical compositions, or even in detergent compositions in general, for example household detergents. The compounds of formula I and their salts have, principally, a very significant foaming power, and a high detergent powder, which are greater than those of N-dodecanoyl-glycyl-glycine described in Japanese patent 84994/1984, as is shown in the experimental portion below.

The compounds of formula I are useful as detergents in media having a pH of 7 to 13 and in particular from 7 to 9.

They can be employed principally as mild detergents in composition having foaming power (cosmetic, hygienic or pharmaceutical compositions for the skin or hair, or for buccodental hygiene or even as emulsifiers in alimentary preparations).

Certain compounds of formula I and their salts can also be employed by man as skin hydration agents, capable principally of reducing water loss from the skin.

These compounds, for example, N-oleoyl glycyl-(D,L) serine, permit then principally to preserve or restore the suppleness of the skin, its elasticity and its barrier function to the entry of toxic substances. It is known that cosmetic or dermopharmaceutical compositions intended for skin hydration (hydrating preparations) are employed by persons having a so-called dry skin. This phenomenon is generally characterized by skin having a rate of evaporation clearly higher than that of healthy skin, by a loss of cutaneous elasticity and by the formation of wrinkles. This phenomenon can be caused principally by pathological disorders of keratinization, by aging or by excessive exposure to the sun or to various external agents (conventional detergents, soaps, solvents, dry atmosphere, etc...). This phenomenon can affect all parts of the body and particularly the face, neck and hands.

Moreover, certain derivatives of formula I can form in water or in aqueous solvents vesicular structures capable of trapping and retaining hydrophobic or hydrophilic substances, and can be employed in this form as vehicles for lipophilic or hydrophilic ingredients, principally in cosmetic, hygienic or pharmaceutical compositions.

The present invention also relates to a cosmetic, hygienic or pharmaceutical composition characterized by the fact that it comprises as an active ingredient at least one derivative of formula I, such as defined above, or a corresponding salt thereof, in a vehicle compatible with application to man on the skin and/or on the hair and/or with the use in the care of buccodental hygiene.

In the compositions of the invention, the derivatives of formula I are present in an amount ranging from 0.05 to 20 percent, and preferably from 0.5 to 10 percent by weight, relative to the total weight of the composition.

The compositions of the invention are principally solutions of the lotion, foaming or non-foaming type; emulsions of liquid or semi-liquid consistency of the milk type, obtained by dispersion of a fatty phase in an aqueous phase or inversely; suspensions or emulsion having a soft consistency of the cream or ointment type; gels; or even solid preparations such as sticks, cleansing cakes or impregnated pads.

The vehicles present in the compositions of the invention are conventional vehicles employed in this type of composition. It is a question, for example, of water and organic solvents compatible with cutaneous use such as, for example, acetone, isopropyl alcohol, ethyl alcohol, triglycerides of $C_6$–$C_{24}$ fatty acids, glycol ethers such as lower alkyl ethers of mono- or dialkylene glycols, the alkylene having, for example, 2 to 4 carbon atoms. There can also be employed, as solvents, esters of polyalkyleneglycol and short chain $C_1$–$C_4$ acids, or even volatile silicones.

The compositions can also contain, the case occurring, fatty bodies, principally natural or synthetic oils.

The compositions of the invention can also include thickening or gelling agents such as cellulose or cellulose derivatives, for example, in an amount ranging from 0.5 to 20 percent by weight relative to the total weight of the composition. The thickening agents can also be constituted by acrylic polymers, alginates, gums such as xanthan, guar or carob gums, gum arabic or even polyethyleneglycols, bentonites and montmorillonites.

The compositions of the invention can also contain other hydrating agents or known humectants, such as glycerine, triacetin, or more generally other active ingredients such as agents active against skin aging.

The compositions of the invention can also contain conventional adjuvants such as anti-oxidant agents, preservative agents, perfumes, dyes, etc.

Among the anti-oxidants, mention can be made of the tert.-butylhydroxyquinone, butylhydroxyanisole, butylhydroxytoluene and α-tocopherol and its derivatives.

The compositions for the skin are principally provided in the form of creams, milks, gels, optionally thickened lotions, foaming solutions for douche or bath, impregnated pads, ointments, sticks or in the form of cakes or hydrating masks.

The compositions for the hair are principally shampoos in which the derivative of formula I or its corresponding salt, can be combined with other surface active agents such as anionic, cationic, nonionic, amphoteric surfactants or mixtures thereof.

The compositions of the invention can also be provided in the form of solutions or dispersions containing derivatives of formula I such as defined above, in vesicular form, the vesicles thus being able to serve as an encapsulation agent for hydrophilic or lipophilic active ingredients, such as retinoic acid, ultraviolet ray filtering agents or even other hydrating agents.

All these compositions are prepared in accordance with conventional procedures.

The compositions of the invention can also be compositions for the care of bucco-dental hygiene, in which the compounds of formula I and/or their salts principally play the role of foaming and cleansing agents. One of the interests of use of these compounds in compositions of this type is their absence of noxiousness. These compositions are, for example, mouth washes or dentifrices. The dentifrices can be provided in the form of pastes or in the form of transparent gels. They contain in addition to at least one surface active agent according to the invention, at least one pulverulent mineral material which acts as a polishing agent, for example, alumina or silica powder. The polishing agent represents, for example, from 10 to 80 percent by weight relative to the total weight of the composition. The dentifrice compositions can also contain cohesion agents, such as natural gums or synthetic thickening agents (principally cellulose derivatives such as methylcellulose, hydroxyalkyl cellulose or the sodium salt of carboxymethyl cellulose). These cohesion agents can be incorporated, for example, in a weight amount ranging up to 10 percent.

The dentifrice compositions can also contain texture and consistency agents, in a weight amount ranging up to, for example, 60 percent. There is employed, for example, as a texture agent, sorbitol, which has moreover, sweetening and anti-bacterial properties.

The composition in the form of mouth washes are liquid compositions which consist essentially of an aqueous solution of a foaming and cleansing surface active agent. In addition to the surfactant according to the invention, these compositions can also contain one or more conventional ingredients such as thickening agents.

The compositions for bucco-dental hygiene, whatever may be their presentation, can contain moreover, in effective amounts, at least one conventional ingredient selected from sweetening agents, aromatization agents, antibacterial agents, sources of fluoride ions, preservatives, etc.

The preparation of dentifrice compositions or mouthwashes, as well as useful ingredients, are well known and described, for example, in the following works: Handbook of Cosmetic Science, H.W. Hibbot Ed. Pergamon Press (Oxford, London, New York, Paris) and Harry's Cosmeticology, Leonard Hill Books (London).

The invention also relates to the use of a derivative of formula I, such as defined above, and/or a corresponding salt, as a surface active agent and/or a hydrating agent in a preparation of cosmetic, hygienic or pharmaceutical composition intended for the treatment or care of dry skin.

Moreover, the invention relates to a process for a cosmetic treatment. intended principally to improve the appearance and elasticity of the skin of persons having dry skin, or intended to prevent the appearance of unesthetic disorders caused by this dry skin phenomenon, characterized by the fact that a cosmetic composition, such as defined above, is applied to the skin of those parts of the body concerned, including optionally the scalp.

The application of the composition of the invention is effected according to known procedures.

The cosmetic treatment process of the invention is applicable as a complement to the treatment of dry dermatoses, ichtiosis, xeroses, etc...xxx The invention also relates to, as a new product, dipeptidic amides of general formula II:

$$R'CO-NHCH_2CONH-CH(CH_2OH)-COOH \qquad (II)$$ 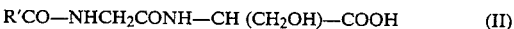

wherein R' represents a linear or branched alkyl, optionally unsaturated, having from 7 to 12 or 14 to 17 carbon atoms, as well as the salts of the compounds of formula (II) and mixtures of the compounds of formula (II) and/or their salts.

It is seen that the compounds of formula (II) correspond to the compounds of formula (I) with the exception of N-tetradecanoyl-glycyl-serine and its salts. The R' group of formula (II) can then have the same meanings as the R group of formula (I) with the exception of $C_{13}$.

The invention also relates to a process for preparing the compounds of formula (II).

This process comprises reacting a serine salt with a compound of formula (III):

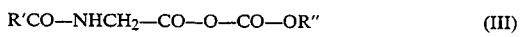

R'CO—NHCH$_2$—CO—O—CO—OR"  (III)

wherein R' is defined above and R" represents ethyl or isopropyl.

The reaction can be carried out principally in a solvent medium such as water/tetrahydrofuran or water/N,N-dimethylformamide mixtures at ambient temperature.

To isolate the product of formula (II) (acid form) either the solvent is evaporated, or an extraction is carried out using an organic solvent such as ethyl acetate. The resulting product is then purified by recrystallization, for example, in a liquid hydrocarbon at ambient temperature.

The starting salt is, for example, an alkaline metal salt or an amine salt such as a triethanolamine salt.

If desired, in accordance with known methods, the compound of formula II can be converted to a corresponding salt.

Supplemental details are given in the experimental portion that follows.

The following non-limiting examples illustrate the invention.

EXAMPLES OF PREPARATION

All the lipodipeptides corresponding to formula I are synthesized according to the following procedure:

A. Preparation of alcanoyl-glycine of formula IV:

R—CO—NH—CH$_2$—COOH  (IV)

wherein R has the same meaning as in formula I.

To 1 equivalent of the selected R-COOH acid, dissolved at a concentration of 25% (weight/volume) in tetrahydrofuran, there are added 1.05 equivalents of triethylamine. This mixture is stirred for 1 hour at ambient temperature and then poured into a round bottom flask containing 1 equivalent of 10% ethyl chloroformate in tetrahydrofuran, at a temperature of −10° C. The reaction medium is left for 3 hours at ambient temperature and then filtered. The filtrate is poured into a sodium glycine salt solution, previously obtained by the addition of 1 equivalent of sodium hydroxide (10% aqueous solution) to 1 equivalent of glycine, while taking care to maintain the pH greater than 9. The mixture is stirred for 3 hours at ambient temperature all while continuing to maintain the pH greater than 9. Concentrated hydrochloric acid is added until a pH equal to 2 is obtained. The reaction mixture is extracted using a 1:1 water/ethyl acetate mixture. The organic phases are dried and concentrated under reduced pressure. The residue is then recrystallized in a solvent selected from heptane, isopropylether, tert. butylmethylether, ethyl acetate or mixtures thereof.

B. Preparation of the derivative of formula I (acid form)

To 1 equivalent of the alkanoyl glycine obtained in the preceding stage, put in solution in 30% of tetrahydrofuran, one add 1.05 equivalents of triethylamine are added. The mixture is stirred for 1 hour at ambient temperature at which point the reaction medium is poured into a 10% ethyl chloroformate solution (or isopropyl chloroformate) (1 eq.) in tetrahydrofuran. The temperature is maintained at −10° C. The reaction mixture is stirred for 3 hours at ambient temperature and then filtered. The filtrate is poured into a serine sodium salt solution prepared by adding 1 equivalent of sodium hydroxide (10% aqueous solution) to 1 equivalent of serine, all while maintaining the pH greater than 9.

The reaction medium is then left at ambient temperature with stirring for 3 hours (while maintaining a pH greater than 9) and then acidified using sufficient concentrated hydrochloric acid to obtain a pH equal to 2. The reaction medium is extracted with the aid of a 1:1 water/ethyl acetate mixture. The organic phases are combined, dried and concentrated under reduced pressure. The residue is recrystallized in a solvent selected from water, heptane, isopropyl ether, tert. butyl methylether, ethyl acetate or mixtures thereof.

C. Preparation of corresponding salts (for example, the sodium or triethanolamine salt)

The salts are obtained by a known method consisting in adding 1 equivalent of sodium hydroxide (10% aqueous solution), or 1 equivalent of triethanolamine, to a 5% solution of the corresponding acid in a 2:1 isopropanol/water mixture at a temperature ranging, for example, from 20° to 70° C. The solution is then concentrated to dryness to obtain the expected salt.

Example 1 —Preparation of N-dodecanoyl-glycyl-(D,L) serine

This product is obtained in accordance with the process described above and is provided in the form of a white powder. It is recrystallized in a water/ethyl acetate mixture.

F=133° C.

| Elemental analysis: C$_{17}$H$_{32}$N$_2$O$_5$.H$_2$O; MW = 362.5 | | |
| --- | --- | --- |
| | C | H |
| Calculated, % | 56.32 | 9.45 |
| Found, % | 55.88 | 8.95 |

The NMR spectrum of the 13C conforms to the indicated structure.

Example 3—Preparation of N-oleoyl-glycyl-(D,L) serine

This product is prepared in a manner analogous to that described in Example 1, and is provided in the form of a white powder. It is recrystallized in a water/ethylacetate mixture.

F=87° C.

| Elemental analysis: C$_{23}$H$_{42}$N$_2$O$_5$: MW = 426.6 | | | |
| --- | --- | --- | --- |
| | C | H | N |
| Calculated, % | 64.76 | 9.92 | 6.57 |
| Found, % | 64.72 | 9.94 | 6.49 |

The NMR spectrum of the 13C conforms to the indicated structure.

Example 3—Preparation of N-linoleoyl-glycyl- (D, L) serine

This product is obtained in an analogous manner, and is provided in the form of a sticky pale yellow solid.

| Elemental analysis: $C_{23}H_{40}N_2O_5$; MW = 424.6 | | | |
|---|---|---|---|
| | C | H | N |
| Calculated, % | 65.06 | 9.50 | 6.60 |
| Found, % | 65.20 | 9.61 | 6.44 |

The NMR spectrum of the 13C conforms to the indicated structure.

Example 4—Preparation of the triethanolamine salt of N-linoleoyl-glycyl-(D,L) serine This salt is prepared in accordance with the procedures described above, and is provided in the form of a yellow paste.

| Elemental analysis: $C_{29}H_{55}N_3O_8 \cdot 0.5H_2O$; MW = 582.8 | | | |
|---|---|---|---|
| | C | H | N |
| Calculated, % | 59.77 | 9.68 | 7.20 |
| Found, % | 59.81 | 9.71 | 7.00 |

Example 5—Preparation of the sodium salt of N-dodecanoyl-glycyl-(D,L) serine

This salt is prepared in an analogous manner and is provided in the form of a white solid.
F=167° C.

| Elemental analysis: $C_{17}H_{31}N_2NaO_5 \cdot 0.5H_2O$; MW = 375.5 | | |
|---|---|---|
| | C | H |
| Calculated, % | 54.37 | 8.59 |
| Found, % | 54.93 | 8.80 |

Example 6—Preparation of the sodium salt of N-oleoyl-glycyl-(D,L) serine

This salt is prepared in accordance with an analogous process, and is provided in the form of a white solid.
F=170° C.

| Elemental analysis: $C_{23}H_{41}N_2NaO_5 \cdot 0.5H_2O$; MW = 457.6 | | | |
|---|---|---|---|
| | C | H | N |
| Calculated, % | 60.36 | 9.25 | 5.02 |
| Found, % | 60.47 | 9.50 | 4.60 |

Example 7—Preparation of the triethanolamine salt of N-dodecanoyl-glycyl-(D,L) serine This salt is prepared in accordance with an analogous procedure, and is provided in the form of a light chestnut colored paste.

| Elemental analysis: $C_{23}H_{47}N_3O_8 \cdot 2H_2O$; MW = 529.6 | | | |
|---|---|---|---|
| | C | H | N |
| Calculated, % | 52.16 | 9.70 | 7.93 |
| Found, % | 51.63 | 9.29 | 7.51 |

Example 8—Preparation of N-octanoyl-glycyl-(D,L) serine

This product is obtained in accordance with a described analogous process. It is recrystallized in an ethylacetate/methanol mixture.
F=97° C.

| Elemental analysis: $C_{13}H_{24}N_2O_5$; MW = 288.4 | | | |
|---|---|---|---|
| | C | H | N |
| Calculated, % | 54.15 | 8.39 | 9.72 |
| Found, % | 54.14 | 8.40 | 9.68 |

The NMR $^{13}C$ spectrum conforms to the indicated structure.

Examples of Cosmetic Composition

Example A—Lotion

A makeup remover lotion having hydrating activity is prepared by mixing the following ingredients:

| N-dodecanoyl-glycyl-(D,L) serine | 2.00 g |
|---|---|
| Antioxidant | 0.05 g |
| Preservative | 0.30 g |
| Isopropanol | 40.00 g |
| Water, sufficient amount for | 100.00 g |

Makeup is removed from the face using a moistened sponge impregnated with this lotion.

Example B—Gel

There is prepared, by admixing the following ingredients, a composition in the form of a gel having hydrating activity:

| N-dodecanoyl-glycyl-(D,L)-serine | 2.00 g |
|---|---|
| Klucel H* | 1.00 g |
| Isopropanol | 40.00 g |
| Preservative | 0.3 g |
| Antioxidant | 0.05 g |
| Water, sufficient amount for | 100.00 g |

This gel is applied, preferably at night, on the face and neck.

*Klucel H is the commercial name of hydroxypropyl cellulose, sold by Hercules.

Example C—Skin care cream (oil-in-water emulsion)

The composition of this cream is the following:

| Sodium salt of N-dodecanoyl-glycyl-(D,L) serine | 3.00 g |
|---|---|
| Glycerol stearate | 2.00 g |
| TWEEN 60 | 1.00 g |
| Cetyl alcohol | 0.50 g |
| Stearic acid | 1.40 g |
| Triethanolamine | 0.70 g |
| Carbopol 940 (neutralized by triethanolamine) | 0.40 g |
| Liquid fraction of karite fat | 12.00 g |
| Synthetic perhydrosqualene | 12.00 g |
| Antioxidant | 0.05 g |
| Perfume | 0.50 g |
| Preservative | 0.30 g |
| Water, sufficient amount for | 100.00 g |

This cream is prepared in the following manner: CARBOPOL 940, neutralized with triethanolamine is added to a portion of the water (85 to 90%) and heated at 25-80° C. There is then added, while stirring, the fatty phase (glycerol stearate, TWEEN 60, stearic acid, cetyl alcohol, liquid fraction of karite fat, perhydrosqualene, antioxidant) heated to the same temperature, the triethanolamine being added last. After 10 minutes of stirring, the dipeptidic derivative and the preservative, previously poured into the remainder of the water are added. At the end of 10 additional minutes, the perfume is added and the stirring is discontinued and the mixture is cooled to ambient temperature.

It is recalled that TWEEN 60 is the commercial name of sorbitan monostearate polyoxyethylenated with 20 moles of ethylene oxide, sold by ICI Americas.

CARBOPOL 940 is the commercial name of an acrylic polymer crosslinked by a polyfunctional agent and sold by Goodrich.

This cream is used for the hydration of the skin.

Example D—A shampoo

This shampoo has the following composition:

| | |
|---|---|
| Sodium salt of N-dodecanoyl-glycyl-(D,L) serine | 10.00 g |
| KLUCEL H | 1.00 g |
| Perfume | 0.50 g |
| Preservative | 0.30 g |
| Water, sufficient amount for | 100.00 g |

To prepare this shampoo, the sodium salt of N-dodecanoyl-glycyl-(D,L) serine is dissolved at 60° C. in sufficient water to produce a clear solution. To this medium there is added an aqueous solution thickened by KLUCEL H, also having a temperature of 60° C. The perfume and the preservative are then added and the final weight is adjusted with water. The composition is then cooled.

Example E—A gel

A gel, intended for bucco-dental hygiene, having the following composition (weight %) is prepared

| Ingredients | % |
|---|---|
| Powdered silica, sold by Degussa under the tradename "SIDENT 9" | 12 |
| Powdered silica, sold by Degussa under the tradename "SIDENT 22 S" | 7 |
| Carboxymethyl cellulose | 0.5 |
| Sorbitol (70% active material) | 66 |
| Dodecyloxycarbonyl glycyl serine neutralized by soda to pH = 2 | 1 |
| Methyl parahydroxybenzoate | 0.2 |
| Sodium monofluorophosphate | 0.8 |
| Sapidity agent, sufficient amount | |
| Dye, sufficient amount | |
| Sweetening agent, sufficient amount | |
| Water, sufficient amount for | 100 |

Foaming Powder Study

This study has been carried out with 5% aqueous solutions (weight/volume) of the compound of Example 5. The comparison product is a 5% solution of compound A (sodium salt of N-dodecanoyl-glycyl-glycine).

The test consists in developing the foam using a brush made of natural hog bristles (length=IS mm) displaced in a plexiglass graduated cylindrical container (inside diameter=35 mm). This container is driven in a uniform circular motion which is the reverse of that described by the brush. This permits a good distribution of the foam in the graduated container despite the small amounts developed. (brush speed=100 rpm, container speed=10 rpm).

The procedure is carried out using 5 ml of each solution studied to which has been added 6 mg of natural feminine sebum.

The foam heights are recorded after one, two and three minutes of stirring.

The results are set forth in Table I

TABLE I

| | Foam Height (cm) at the end of a time of | | |
|---|---|---|---|
| Compound | 60 sec | 120 sec | 180 sec |
| A | 11.25 | 13.75 | 20 |
| Ex. 5 | 12.5 | 21.25 | 28.75 |

In this test, the hydrating effect is evaluated by measuring the reduction of water loss of human stratum corneum previously delipidated. The stratum corneum is delipidated for one hour with a 2:1 dichloromethane/methanol mixture.

This test is effected in accordance with a method analogous to that described by J.L. Leveque et coll., J. Soc. Cosmet. Chem., 30, 333-343 (1979).

The following procedures are carried out:

The water flow $(g/m^2.H)$ traversing a sample of stratum corneum placed below a water reservoir is measured. Using an evaporimeter (Servomed, registered mark), the evaporation values before and after treatment are registered, and the eventual reduction of the insensible loss of water is thus determined.

The treatment consists in applying on the sample of stratum corneum 10 μl of a 3% solution in a 2:1 dichloromethane: methanol mixture of the compound being studied. The measurements are carried out 3 hours after this treatment.

On the basis of this test the compound of Example 2 is compared with N-oleoyl-glycyl-glycine (compound B) and with the solvent (2:1 dichloromethane:methanol) alone.

The results are set forth in Table II.

TABLE II

| Compound Studied | Reduction of the insensible loss of water |
|---|---|
| B | 6% ± 3 |
| Example 2 | 32% ± 3 |
| Solvent | 6% ± 3 |

I claim:

1. A dipeptide amide having the formula
RCO—NHCH$_2$CONH—CH(CH$_2$OH)—COOH    (I)
wherein RCO- represents an oleoyl group or salts thereof.

* * * * *